US00PP18840P2

(12) United States Plant Patent
Kordes

(10) Patent No.: US PP18,840 P2
(45) Date of Patent: May 27, 2008

(54) MINIATURE ROSE PLANT NAMED 'KORPOLARE'

(50) Latin Name: *Rosa hybrida*
Varietal Denomination: KORpolare

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 11/704,616

(22) Filed: Feb. 10, 2007

(51) Int. Cl.
*A01H 5/00* (2006.01)

(52) U.S. Cl. ..... Plt./122
(58) Field of Classification Search ..... Plt./122
See application file for complete search history.

*Primary Examiner*—Annette H Para

(57) ABSTRACT

A new and distinct variety of miniature rose with long lasting, novel red flowers, and abundant dark green and attractive foliage. It exhibits compact, uniform growth and flowering under greenhouse conditions when grown as a potted floral plant. The new variety propagates well from cuttings and by grafting. This new and distinct variety has shown to be uniform and stable in the resulting generations from asexual propagation.

1 Drawing Sheet

Genus, species and Variety denomination: The botanical classification of the new rose plant is *Rosa hybrida,* 'KORpolare'.

BACKGROUND OF THE INVENTION

The new variety of miniature rose plant of the present invention originated from a controlled crossing in a breeding program between 'KORkleiva', a patented rose described and illustrated in U.S. Plant Pat. No. 11,232 issued on Feb. 22, 2000, and 'Poulrac' a patented rose described and illustrated in U.S. Plant Pat. No. 11,543 issued on Oct. 3, 2000.

The two parents were crossed and the resulting seeds were planted in a controlled greenhouse environment. The resulting seedlings exhibited distinctive physical and biological characteristics. The new rose plant was selected in as a single plant from the seedling beds due to its superior characteristics and asexually propagated for further evaluation. This new and distinctive miniature rose variety is named 'KORpolare'.

SUMMARY OF THE INVENTION

The new rose plant may be distinguished from its seed parent, 'KORkleiva', by the following combination of characteristics:

1. 'KORpolare' has dark red flowers while 'KORkleiva' has cream white flowers,
2. 'KORpolare' has an average of 55 petals, white 'KORkleiva' has 25 to 30 petals.

The new rose plant may be distinguished from its pollen parent, 'Poulrac' by the following combination of characteristics:

1. 'Poulrac' has small flowers with few petals and 'KORpolare' has medium to large sized flowers with numerous (very double) petals.
2. 'Poulrac' has medium sized leaves of average abundance while 'KORpolare' has larger leaves with above average abundance.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers on upright stems;
3. Resistance to diseases encountered in greenhouse and nursery culture; and
4. Suitability for production from softwood cuttings in floral and nursery containers;

This combination of qualities is not present in prior rose cultivars. These objectives have been substantially achieved and in that distinguish 'KORpolare' from all other varieties of which we are aware.

As part of the rose development program, Tim-Hermann Kordes germinated the seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpolare' was selected in May, 2000 from the seedling beds to be asexually propagated for further evaluation. The first asexual reproduction of 'KORpolare' was done by rooting softwood cuttings in July, 2000 at the Rosa-Danica Nursery in Odense, Denmark.

This initial and other subsequent propagations conducted in controlled environments show that the foregoing and all other characteristics of 'KORpolare' come true to form and are transmitted through succeeding generations.

BRIEF DESCRIPTION OF THE DRAWING

The accompanying color illustration shows as true as is reasonably possible to obtain in color photographs of this type, the typical characteristics of flower buds, flowers, sepals, several stems and a leaf of 'KORpolare'.

DETAILED BOTANICAL DESCRIPTION

The following is a description of 'KORpolare', as observed in its growth in April, 2006 in a nursery in Jackson County, Oreg. on plants of 6 months of age. Color references are made using The Royal Horticultural Society (London, England) Colour Chart, 2001 except where common terms of color are used.

For a comparison, several physical characteristics of the rose variety 'Poulhappy', a patented rose variety described and illustrated in U.S. Plant Pat. No. 9,483 and issued on Mar. 26, 1996 are compared to 'KORpolare' in Chart 1.

CHART 1

| | 'KORpolare' | 'Poulhappy' |
|---|---|---|
| Color, upper side of petals | Red Group 53B. | Red Group 46B. |
| Average petal count | 55 petals. | 25-30 petals. |

Parents:

*Seed parent.*—'KORkleiva'.

*Pollen parent.*—'POULrac'.

Classification:

*Botanical classification.*—*Rosa hybrida,* 'KORpolare'.

*Commercial classification.*—Miniature rose.

FLOWER AND FLOWER BUD

Blooming habit: Continuous.

*Flower bud.*—Size: Upon opening, 12 mm in diameter and 25 mm in length from base of receptacle to end of bud. Bud form: Ovate and long. Bud color: As sepals first unfold, bud color is Red Group 53C. When ¼ open, the bud color is Red Group 53B. Sepals: Size: Average 35–40 mm long×9 mm wide. Shape: Sepals generally subulate. Sepal apex is generally cirrose. Moderately strong foliaceous appendages on three of the five sepals. Base is flat at union with receptacle. Quantity: Five. Surface texture: Upper surface covered in fine hairs. Lower surface with moderate numbers of fine hairs. Stipitate glands are present on the lower surface and the sepal margins. Color: Upper surface Green Group 137B. Lower surface Green Group 138A.

*Receptacle.*—Surface: With small, fine, white hairs and stipitate glands. Color: Yellow-Green Group 144A. Shape: Urn shaped. Size: 7 mm (h)×7 mm (w).

*Peduncle.*—Surface: With fine hairs and stipitate glands. Length: 45 to 50 mm average length from top of node to receptacle. Diameter: 1.75–2.25 mm average diameter. Color: Yellow-Green Group 146B with intonations of Greyed-Red Group 181B. Strength: Strong. Borne: Most frequently, borne singly with one flower bud per flowering stem. Infrequently, two to three flower buds.

Flower bloom:

*Fragrance.*—Little to none.

*Duration.*—Long lasting. A blooming plant with flowers has a commercial shelf life of 25–30 days. The blooms have a duration on the plant of approximately 21 to 24 days.

*Size.*—Medium to large to a 10 cm pot rose. Average flower diameter is 55–60 mm when open. Average flower height is 25–30 mm from base of receptacle to top of open bloom.

*Form.*—Globular. Shape of flower when viewed from the side: Upon opening, upper part: Flattened convex. Upon opening, lower part: Flattened convex. Open flower, upper part: Flattened convex. Open flower, lower part: Concave.

Color:

*Upon opening, petals.*—Outermost petals: Outer Side: Red Group 53B. Inner Side: Inner Side Red Group 46A. Innermost petals: Outer Side: Red Group 53D. Inner Side: Red Group 53B.

*Upon opening, basal petal spots.*—Basal petal spot, outermost petals: Outer Side: Green-Yellow Group 1C. Inner Side: Green-Yellow Group 1C. Basal petal spot, innermost petals: Outer Side: Green-Yellow Group 1D. Inner Side: Green-Yellow Group 1D.

*After opening, petals.*—Outermost petals: Outer Side: Red Group 53A. Inner Side: Red Group 53A with intonations of Red-Purple 60A. Innermost petals: Outer Side: Red Group 53C. Inner Side: Red Group 53A–B with Red fading over time to 45B.

*After opening, basal petal spots.*—Basal petal spot, outermost petals: Outer Side: White group 155C. Inner Side: Green-White Group 157D. Basal petal spot, innermost petals: Outer Side: Green-Yellow Group 1B. Inner Side: Green-Yellow Group 1A. Variegations: Some petals exhibit a vertical white intonation near the middle of petal. Color: Green-White 157D.

General Tonality: On open flower Red Group 53-A–B with intonations of Red-Purple 60A. No change in the general tonality at the end of the day. Afterwards, general tonality is Group 53 A–B with intonations of Red-Purple 60A.

Petals:

*Petal count.*—Approximately 55 petals under normal conditions.

*Petal reflex.*—Petals reflex strongly.

*Petal edge.*—Slightly ruffled with mature petals relaxing to point in center of margin.

*Petal shape.*—Apex shape is round. Shape of base is rounded.

*Petal size.*—30 mm long. 30–35 mm wide.

*Thickness.*—Average.

*Petal arrangement.*—Generally in a regular pattern with overlapping edges.

*Petaloids.*—Present. Average of 8–12 per flower. Petaloids are 10–12 mm long and 16–18 mm wide. Color of inner side is Red Group 53B. Color of outer side is Red Group 53B. Surface texture is smooth. Shape is linear to elliptic.

Reproductive Organs:

*Pistils.*—Approximately 85–95 present. Stigmas: Location: Slightly superior in location to anthers. Color: Green-Yellow Group 1D. Styles: Length: 1.3 mm long. Color: Green-Yellow Group 1D. Slight intonations of Red-Purple Group 70 C-D.

*Stamens.*—Approximately 80 on average and regularly arranged. Anthers: Size: 2.5 mm long. Color: Yellow-Orange Group 20A. Pollen: Generally present. Color: Yellow-Orange Group 20A. Filaments: Color: Yellow-Green Group 1A. Length: 5 mm.

THE PLANT

*Plant growth.*—Vigorous. Bushy to upright habit. When grown as a 10 cm pot plant, the average height of the plant is 20 cm and the average width is 16–18 cm.

*Stems.*—Stem color: Young wood: Yellow-Green Group 146A-B. Older wood: Yellow-Green Group 144A. Stem surface: Young wood: Smooth. Older wood: Smooth.

*Prickles.*—Present. Incidence. 5 per 10 cm of stem. Size: Average length: 4 mm. Color: Juvenile prickles Greyed-Purple Group 183D. Mature prickles Greyed-Red Group 179C. Shape: Linear to slightly downward hooked.

*Leaves and leaflets.*—Normally 5 leaflets on normal leaves in middle of the stem. Leaf size: 30–35 mm (l)×21–25 mm (w). Abundance: Above average. Texture: Semi glossy. Smooth. Color, mature foliage: Upper Leaf Surface: Green Group 139A. Lower Leaf Surface: Green Group 138B. Color, juvenile foliage: Upper Leaf Surface: Green Group 139A. Lower Leaf Surface: Green Group N 138B. Anthocyanin intonations: Intonations of Greyed-Purple Group 183C present on leaf margins, developing leaves, and juvenile stems on plants grown under high light conditions.

*Stipules.*—Size: 12–13 mm (l) — 3 mm (w). Stipule color: Green Group 137B. Presence of stipitate glands: Present on margins. Margins: Bearded. Serrated.

*Petiole.*—Length: 12 mm–15 mm. Diameter: 1–1.5 mm average diameter. Petiole color: Above: Green Group 137A. Underneath: Yellow-Green Group 146B. Anthocyanin: Present Greyed-Purple Group 183D. Prickles: Limited numbers. Small. Stipitate glands: Few to none.

*Petiole rachis.*—Color: Above: Green Group 137 B-C Underneath: Yellow-Green Group 146C. Prickles: Limited numbers. Small. Stipitate glands: Few to none.

*Leaflets.*—Size: Average size of the terminal leaflet is 40 mm (l)×22 mm (w). Shape: Ovate. Margins: Serrated. Texture: Leathery.

Hips/Seed formation: None observed. The plant has not been grown to the stage of hip and seed development due to its use as a flowering potted plant.

Winter hardiness: To date, the plant has been grown successfully in USDA Zone 7.

Disease resistance: Above average to excellent resistance to mildew and *Botrytis* under normal growing conditions in Jackson County, Oreg.

I claim:

1. A new and distinct variety of miniature rose plant characterized by the following combination of characteristics:

(a) forms abundant, attractive long lasting red flowers;

(b) exhibits a compact and bushy growth habit;

(c) is suited for growing in greenhouse in pots from softwood cuttings, and;

(d) exhibits durable flowers and foliage suitable for distribution in the floral industry;

substantially as herein illustrated and described.

* * * * *

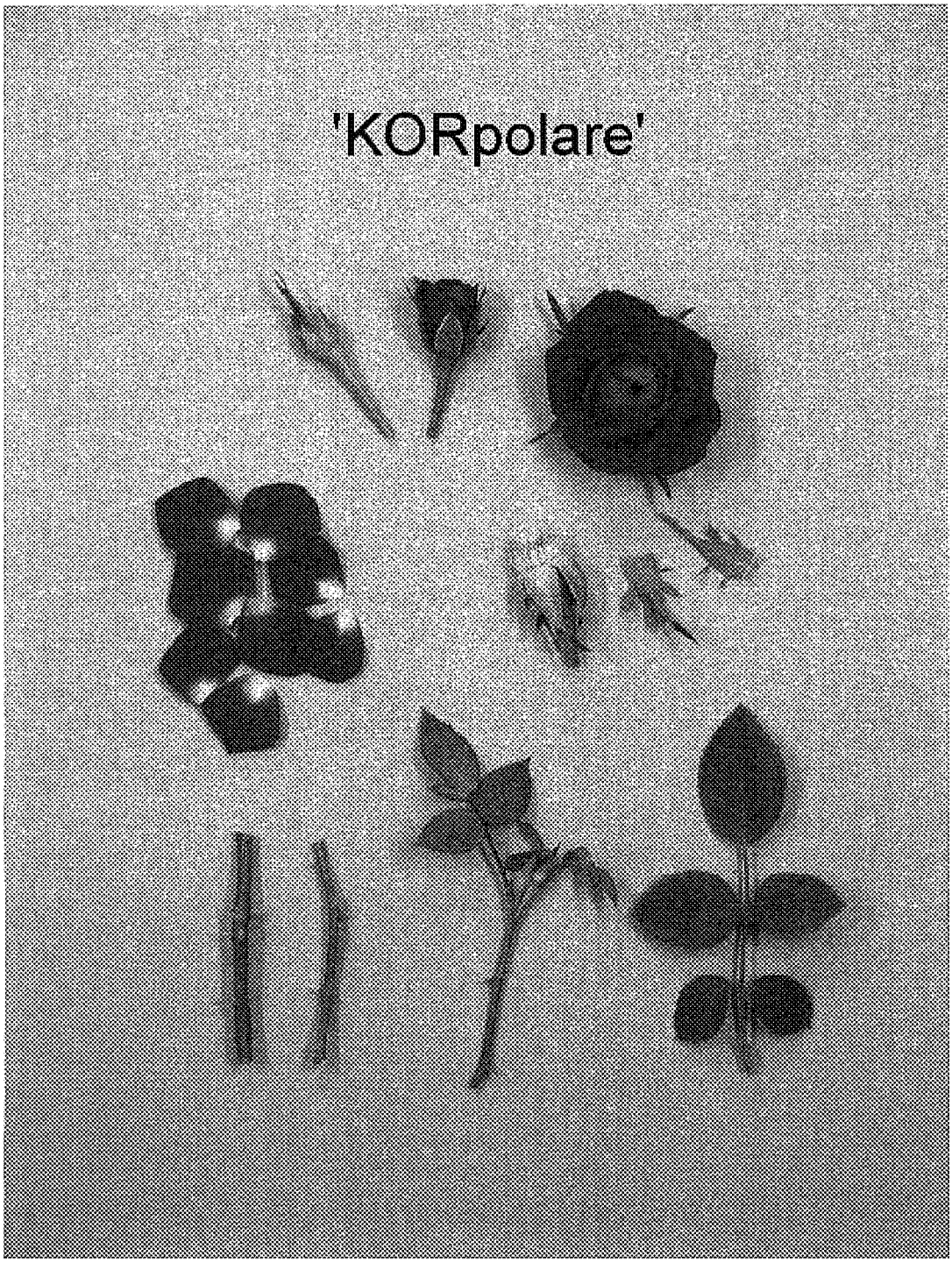
'KORpolare'